US010629296B2

(12) United States Patent
Soon-Shiong et al.

(10) Patent No.: US 10,629,296 B2
(45) Date of Patent: Apr. 21, 2020

(54) MOBILE CARRIER-CENTRIC DATA RECORD CUSTODIAN SYSTEMS AND METHODS

(71) Applicant: NANTHEALTH, INC., Culver City, CA (US)

(72) Inventors: Patrick Soon-Shiong, Culver City, CA (US); Ravi Seshadri, Plano, TX (US); Nicholas J. Witchey, Laguna Hills, CA (US)

(73) Assignee: NANTHEALTH, INC., Culver City, CA (US)

( * ) Notice: Subject to any disclaimer, the term of this patent is extended or adjusted under 35 U.S.C. 154(b) by 948 days.

(21) Appl. No.: 14/838,264

(22) Filed: Aug. 27, 2015

(65) Prior Publication Data

US 2016/0063189 A1 Mar. 3, 2016

Related U.S. Application Data

(60) Provisional application No. 62/043,847, filed on Aug. 29, 2014.

(51) Int. Cl.
*G06F 19/00* (2018.01)
*G16H 10/65* (2018.01)
*H04L 9/00* (2006.01)

(52) U.S. Cl.
CPC ............ *G16H 10/65* (2018.01); *H04L 9/008* (2013.01); *H04L 2209/88* (2013.01)

(58) Field of Classification Search
USPC ........................................................ 705/2–4
See application file for complete search history.

(56) References Cited

U.S. PATENT DOCUMENTS 8,126,728 B2 * 2/2012 Dicks .................. A61B 5/0022
705/2
2008/0059227 A1 3/2008 Clapp
(Continued)

FOREIGN PATENT DOCUMENTS

WO WO 2013/163686 11/2013
WO WO 2014/059222 4/2014

OTHER PUBLICATIONS

Busis, Neil. "Mobile phones to improve the practice of neurology." Neurologic clinics 28.2 (2010): 395-410.*
(Continued)

*Primary Examiner* — Mark Holcomb
(74) *Attorney, Agent, or Firm* — Stetina Brunda Garred and Brucker

(57) ABSTRACT

A system for mobile carrier-centric data record custodians is provided and includes cellular network interfaces that transmit and receive wireless communication over a cellular network, an electronic medical record (EMR) database that stores EMRs, and a mobile account management server coupled with the cellular network interfaces and the EMR database, the mobile account management server receiving an EMR request associated with a mobile user account over the cellular network, querying the EMR database for a results set having EMRs satisfying the query, generating a plurality of EMR responses to the EMR request as a function of the results set and state information associated with the cellular network, and transmitting the plurality of EMR responses over the plurality of cellular network interfaces to the mobile device via the cellular network, the plurality of EMR responses being formatted for wireless protocols of the cellular network interfaces over which they are transmitted.

38 Claims, 7 Drawing Sheets

(56) References Cited

U.S. PATENT DOCUMENTS

| | | | | |
|---|---|---|---|---|
| 2008/0095049 A1* | 4/2008 | Bugenhagen | .......... | H04L 67/141 370/229 |
| 2012/0232929 A1* | 9/2012 | Experton | ............... | G06Q 10/06 705/3 |
| 2013/0054272 A1 | 2/2013 | Rangadass et al. | | |
| 2013/0304512 A1* | 11/2013 | Seshadri | ............... | G06F 19/322 705/3 |
| 2014/0122096 A1* | 5/2014 | Berry | ..................... | G16H 10/60 705/2 |
| 2014/0207686 A1* | 7/2014 | Experton | ............ | G06F 19/3418 705/51 |
| 2014/0344153 A1* | 11/2014 | Raj | .................... | G06Q 20/3821 705/44 |

OTHER PUBLICATIONS

PCT International Search Report and Written Opinion in PCT International Application Serial No. PCT/US2015/047509 dated Nov. 27, 2015.

Lim, Hyung Gun, "International Preliminary Report on Patentability," PCT/US2015/047509, dated Dec. 19, 2016, International Application Division, Korean Intellectual Property Office, Daejeon, Republic of Korea, 12 pages.

* cited by examiner

MOBILE CARRIER-CENTRIC DATA RECORD CUSTODIAN SYSTEMS AND METHODS

CROSS-REFERENCE TO RELATED APPLICATION

This application claims the benefit of priority under 35 U.S.C. § 119(e) to U.S. Provisional Patent Application Ser. No. 62/043,847, filed on Aug. 29, 2014 and entitled MOBILE CARRIER-CENTRIC DATA RECORD CUSTODIAN SYSTEMS AND METHODS, the disclosure of which is hereby incorporated by reference in its entirety.

TECHNICAL FIELD

This disclosure relates in general to the field of healthcare systems and, more particularly, to systems and methods related to mobile carrier-centric data record custodians.

BACKGROUND

The background description includes information that may be useful in understanding the present disclosure. It is not an admission that any of the information provided herein is prior art or relevant to the disclosure, or that any publication specifically or implicitly referenced is prior art.

Electronic medical record (EMR) ecosystems are heavily burdened by jurisdictional regulations, complicated standards, or proprietary formats all of which represent good intentions that has been implemented for the sake of the patient or other consumer. Unfortunately these efforts have created a complicated, tangled web of EMR data beyond the ability of non-technical consumers to manage. For example, a patient's EMRs could be located across myriad servers, stored in different formats, or are just inaccessible to the patient because that patient lacks authorization to access the patient's own data on a server owned by others (e.g., personal physicians, pharmacies, hospitals, insurance companies, etc.). Thus, a patient is unable to collect the patient's own data or share the patient's own information with other healthcare stakeholders.

A great deal of effort has been directed to creating centralized or even decentralized EMR management systems to ease access to patient data. Interestingly, the problem with EMR data management is not just a global ecosystem issue, but also infects departments within individual healthcare organizations. For example, one such centralized effort targets collecting healthcare data from disparate clinical systems of a healthcare organization into a centralized location. In such an approach, the patient lacks easy access to the patient's data and healthcare stakeholders outside an individual healthcare organization lacks easy access to the patient's data.

A better approach would place the patient in a more central role in the management of the patient's own data. Still, migration toward a patient-centric system has been slow, although there has been some progress toward allowing patient's to conduct some level of healthcare interactions via mobile phones. For example, a virtual pharmacy can facilitate interaction with a patient through a mobile phone application. Although patient can access the virtual pharmacy, the virtual pharmacy remains the central point of communication among stakeholders with respect to the patient's pharmacy needs. Such an approach fails to provide guidance toward facilitating access to a patient's EMR data no matter the affiliation of the stakeholder.

From the perspective of a private practice, practices can distribute EMRs to mobile devices. In various known examples, one or more practices operate as a hub for EMR data among stakeholders. EMR information may be presented on a cell phone, but such approaches fail to appreciate the complexity that could be involved with healthcare transactions in a patient centric model, especially when multiple practices are involved.

One aspect of the complexity of managing healthcare transactions includes making payments with respect to healthcare services. For example, a known healthcare payment system collects a price list for one or more healthcare services offered by a provider and transmits the price list to a mobile device of the patient. Upon authorization by the patient, the healthcare payment system renders payment via one or more funding source accounts. Although the approach provides some flexibility to the patient, the healthcare payment system becomes another layer of complexity in the ecosystem, which further distances a patient from access to the patient's data.

In a somewhat similar approach, payment is authorized for medical services via a mobile device via an "H-Wallet". Another approach provides an intermediary service that manages a user's request for payment of a healthcare bill. In both cases, the healthcare payment systems function as an intermediary; yet another layer of complexity.

Although the examples listed above seek to improve a user's experience with respect to the management of healthcare data via a mobile phone, they all introduce additional layers of complexity that further distance a patient from the patient's healthcare data. The approaches above fail to take into account possible shifts in the healthcare market where healthcare services become heavily commoditized or are provided as a retail service. In such a retail market environment, there will be little tolerance for numerous layers of complexity. Rather, the patient may have to take on a greater role with respect to being the central hub for the patient's healthcare data. Still, the patient may desire some form of healthcare custodian.

A healthcare data custodial ecosystem as described herein according to various embodiments that can be provided by one or more mobile carriers. In such scenarios the mobile carriers operates as a healthcare data custodian and can provide direct access to EMR data to the patient or other stakeholders without intermediaries or complexity. Thus, there remains a need to provide data custodial services via one or more mobile carriers.

Note that all publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

SUMMARY

A mobile carrier-centric data record custodian system comprises a plurality of cellular network interfaces configured to transmit and receive wireless communication over a cellular network, an electronic medical record (EMR) database configured to store a plurality EMRs indexed at least according to mobile user accounts, and a mobile account management server coupled with the cellular network interfaces and the EMR database. The mobile account management server receives an EMR request associated with at least one mobile user account over the cellular network, queries the EMR database for a results set having EMRs satisfying the query and as a function of the mobile user account, generates a plurality of EMR responses to the EMR request as a function of the results set and state information associated with a mobile device, the cellular network, and the mobile user account, and transmits the plurality of EMR responses over the plurality of cellular network interfaces to the mobile device via the cellular network, each one of the plurality of EMR responses being formatted for a specific wireless protocol corresponding to a respective cellular network interface over which it is transmitted.

The cellular network interface couples with one or more of various wireless networks, including GSM, EDGE, HSPA, HSPA+, TD-LTE, CDMA, UMTS, WiMAX, EVDO, and WiFi, with different cellular network interfaces coupling with correspondingly different wireless networks. Examples of the mobile device include a smart phone, a vehicle, a robot, a tablet, a medical device, a sensor, a device server, a point of sales terminal, a kiosk, a vehicle, and a tablet. Note that in some embodiments, the EMR database may be coupled with the plurality of cellular network interfaces.

In some embodiments, the EMR database includes a clinical operating system (cOS) service. In some embodiments, the mobile account management server itself includes a clinical operating system. In such embodiments, the EMR request adheres to a protocol of the clinical operating system. For example, the EMR request can include one or more of a monitoring service request, an alert request, a workflow request, a business service request, a routing services request, a validation request, a discovery service request, a consent services request, and an event services request. The mobile account management server may be further configured to provide access to the clinical operating system via an application program interface (API). The API may be published via at least one of the plurality of cellular network interfaces. In some embodiments, the API may include a web service API.

In some embodiments, the EMR request may include a healthcare services transaction, for example, a request for a service, a location of a service, a cost of a service, a service authorization, a service authentication, a healthcare provider request, and a service adjudication. In some embodiments, the EMR request may include a healthcare goods transaction, for example, a healthcare product purchase, a prescription, and a healthcare product lease. In some embodiments, the EMR request may include a records transaction, for example, a record write transaction, a record read transaction, a record create transaction, a record delete transaction, and a record modify transaction.

In some embodiments, the EMR request may include healthcare context data, for example, including a contextual representation of the mobile device, a patient, a healthcare provider, a service, a product, a location, or an event. In such embodiments, the mobile account management server may be configured to generate the plurality of EMR responses as a function of the healthcare context data. Examples of healthcare context data includes an absolute location of the mobile device, a relative location of the mobile device, a time of the EMR request, a patient identifier, a healthcare provider identifier, a weather condition at a location of the mobile device, a traffic condition around a location of the mobile device, an urgency, a priority, a certification requirement, a relationship requirement, etc.

In some embodiments, the EMRs include patient records. In other embodiments, the EMRs include healthcare provider records. In yet other embodiments, the EMRs include employer healthcare records. In yet other embodiments, the EMRs include employee healthcare records. In some embodiments, at least one of the EMR responses includes a payment authorization request associated with the mobile user account. In other embodiments, at least one of the EMR responses can include a payment to an account associated with the mobile device.

In some embodiments, the EMR database may be configured to store the plurality of EMRs according to a secured format, for example, that adheres to a cryptographic standard and depends on the mobile user account. The secured format may also, or alternatively, adhere to a secure function that depends on a patient's authentication key. In some embodiments, the secured format may include a homomorphic encryption format. In some embodiments, an analytics engine may be coupled with the mobile account management server, for example, to compile analytics based on the results set and wherein the plurality of EMR responses includes the analytics.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Figure 1:
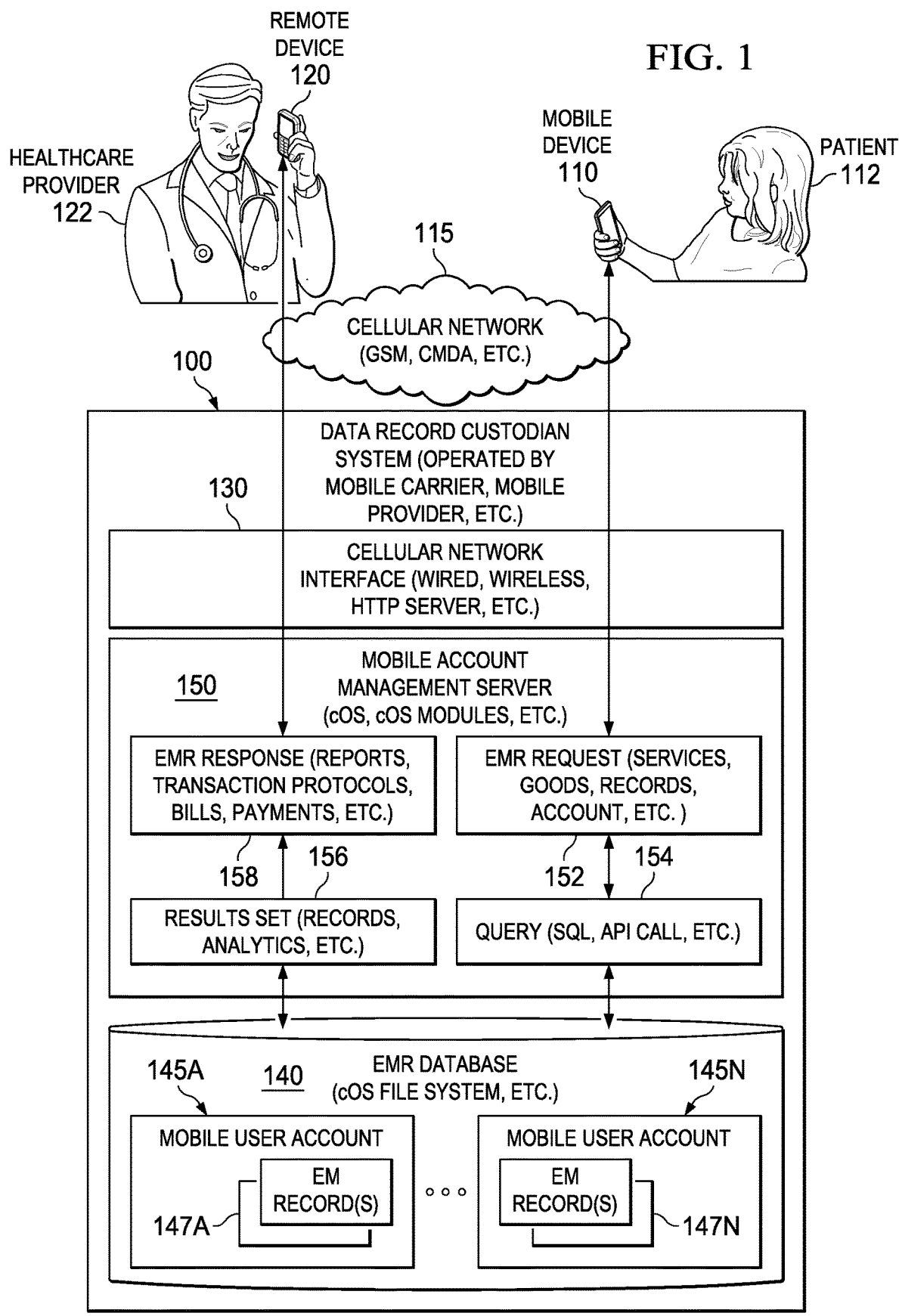
FIG. 1 is a simplified block diagram illustrating a system related to patient mobile carrier-centric data record custodians according to an example embodiment.

Turning to FIG. 1, FIG. 1 is a simplified block diagram illustrating a system 100 related to mobile carrier centric data custodians according to an example embodiment. FIG. 1 presents a schematic overview of a healthcare custodian ecosystem where data record custodian system 100 is hosted or otherwise managed by a mobile carrier (e.g., mobile network operator, wireless service provider, mobile network carrier, cellular company). Data record custodian system 100 includes EMR database 140 storing EMRs associated with mobile users. Data record custodian system 100 brokers access to the EMRs via mobile account management server 150, for example, in response to one or more EMR requests made by various stakeholders, such as a patient 112 or a healthcare provider 122. One of the advantages of having a mobile carrier or mobile provider operate as an EMR custodian, such as data record custodian system 100, is that patient 112 can authorize healthcare payments via mobile accounts (e.g., cell phone accounts, wireless carrier accounts). The mobile carrier can provide a single itemized bill to patient 112 listing mobile charges and healthcare charges.

Data record custodian system 100 comprises a mobile carrier system (operated by a mobile carrier, mobile provider, etc.) that includes one or more cellular network interface 130, one or more mobile account management server 150, and one or more EMR database 140. Cellular network interface 130 comprises physical communication components configured to couple with at least one or more mobile device 110 over cellular network 115. Example cellular networks 115 can include Global System for Mobile Communications (GSM™), EDGE® (Enhanced GPRS), High Speed Packet Access (HSPA), HSPA+, Code Division Multiple Access (CDMA), time division Long-Term Evolution (TD-LTE), Universal Mobile Telecommunications System (UMTS), Evolution Data Only (EVDO), or other type of cellular network. The nature of cellular network 115 can depend on where data record custodian system 100 is deployed. For example, if data record custodian system 100 is deployed in India, cellular network 115 could operate one or more of the following technologies: GSM, EDGE, HSPA, HSPA+, TD-LTE, or other operating network technology. In some embodiments, cellular network interface 130 may not be required to directly connect to cellular network 115. For example, cellular network interface 130 could indirectly interface to cellular network 115 via alternative network technologies, such as wireless (e.g., WiFi, WiMAX, etc.) or wired (e.g., Ethernet, ATM, PSTN, etc.).

Mobile device 110 and remote device 120 comprise computing devices capable of communicating with mobile account management server 150 over cellular network 115. From the perspective of patient 112, mobile device 110 could include a suitably provisioned smart phone, for example, provisioned with an application ('app') that configures the smart phone to interact with mobile account management server 150. In various embodiments, mobile device 110 or remote device 120 may comprise other patient-centric devices such as, by way of examples and not as limitations, a vehicle (e.g., ambulance, etc.), a healthcare robotic assistant, a medical device (e.g., blood pressure monitor, EKG, EEG, etc.), a sensor (e.g., Pulse-Oximeter, thermometer, galvanometer, etc.), a device server.

A device server represents a network device that converts data obtained from a legacy device into a proper protocol format for transmission over a network. Example cellular device servers include the Digi® Connect™, Lantronix® PremierWave®, or Moxa® OnCell™. Additionally, remote device 120 associated with healthcare provider 122 could comprise be a smart phone. From a healthcare provider perspective, remote device 120 could include, by way of examples and not as limitations, a point of sales terminal, a kiosk, a vehicle, a tablet, or other point-of-care device. It should be appreciated that, although mobile device 110 and remote device 120 are illustrated as being differentiated types of devices based on their roles, the devices could be the same type of device.

Mobile account management server 150 comprises one or more computer servers configured or programmed to operate as a request broker within the mobile carrier environment. In some embodiments, mobile account management server 150 is provisioned with a clinical operating system (cOS™), through which mobile account management server 150 is able to take on the roles or responsibilities disclosed herein. A suitable cOS that can be adapted for use with the disclosed technologies includes those offered by Nant Health, LLC (see URL nanthealth.com/cos-clinical-operating-system/). Various aspects of a cOS are also describe in co-owned U.S. patent applications publications 2010/0037067; 2011/031378; 2013/0054272; 2013/0144653; 2013/0166317; 2013/0304512; and 2013/0304496, the disclosures of which are incorporated herein in their entireties. In such embodiments, mobile account management server 150 is configured or programmed to provide access to the cOS services or systems via one or more application program interfaces (APIs). The APIs can be published to cOS service consumers (e.g., mobile device 110, remote device 120, medical devices, etc.) over cellular network interface 130, for example, in the form of a consumable web services API.

EMR database 140 comprises one or more computing storage devices configured or programmed to store EMRs 147A through EMRs 147N, collectively referred to as EMRs 147. EMRs 147 are indexed at least according to corresponding mobile user accounts 145A through 145N, collectively referred to as mobile user accounts 145. In an example embodiment, mobile user account 145A might correspond to patient 112 while mobile user account 145N might correspond to healthcare provider 122. Although EMRs 147 are indexed at least by mobile user accounts 145, EMRs 147 could also be indexed by other attributes, such as, by way of examples and not as limitations, demographic attributes, location attributes, conditions attributes, goods or services attributes, ailment attributes, prescription attributes, lab study attributes, genomic attributes, or other attributes. In some embodiments, EMRs 147 can also include electronic health records (EHRs), and vice versa.

EMR database 140 could also comprise a cOS service through which it is able to provide access to EMRs 147. Similar to mobile account management server 150, EMR database 140 can also offer its services as an API to other devices over a network (e.g., cellular network 115). For example, EMR database 140 could include a HTTP server front-end that brokers web services APIs through which queries can be submitted. In some embodiments, the query comprises a mobile user account identifier (e.g., phone number, social security number, universal health identifier, an AADHAAR number, etc.) along with one or more contextual attributes packaged as an XML, JSON, or YAML data stream submitted to the HTTP server. EMR database 140 can also be implemented based on a relational database (e.g., MySQL, etc.) or even a graph database (e.g., Neo4J, etc.) in embodiments where relationship information is important (e.g., social relationships, stakeholder relationships, medical condition relationships, etc.) and are used to index EMRs 147.

EMR database 140 and mobile account management server 150 may exist within a cOS environment as discussed above. In such embodiments, the stakeholders would still benefit from securing their EMRs 147. Thus, EMR database 140 can be further secured to store EMRs 147 according to one or more secured formats. The secured formats can include quite a broad spectrum of possible data storage formats. In some embodiments, the format can adhere to one or more cryptographic standards where EMRs 147 are collectively or individually encrypted based on one or more keys. For example, EMRs 147 could be encrypted individually within a non-encrypted file system according to AES, or other secure function, according to patient 112's public or private key, which can depend on the stakeholder's corresponding mobile user account 145. Further, EMRs 147 could also be stored within a secured file system where the file system structure itself is secured, for example according to FSFS (see URL fsfs.sourceforge.net) or other secured file system.

In other or additional embodiments, EMR database 140 and mobile account management server 150 can also be elements that exist within a homomorphic encryption space where data exchanges or data storage adhere to a homomorphic encryption format. Thus, a stakeholder's key can provide access to personalized homomorphic encryption space in which EMRs 147 are stored or processed. This approach can facilitate a commoditized healthcare market because each stakeholder could essentially have a private healthcare EMR cloud existing within the mobile carrier's infrastructure. Even though the mobile carrier's infrastructure hosts the personalized EMR cloud, the mobile carrier itself does not necessarily have access to the unencrypted EMRs 147 while also being able to process EMRs 147 in a meaningful fashion "outside" the stakeholder's homomorphic encryption space.

EMRs 147 can include a wide variety of data records, which can vary from stakeholder to stakeholder. From the perspective of patient 112 having corresponding EMRs 147A, EMRs 147A could include numerous health records, for example, covering the entire life span of patient 112. The health records could include lab results, pharmacy receipts, compliance data, prescription records, birth certificates, family registers, biometric data (e.g., historical, real-time, trends, etc.), genome information, transaction histories, personal alerts or notification triggers, or other types of records. In a retail healthcare market such health records might also include images or other digital representations of paper-based records. For example, the records could include images of receipts or lab reports where patient 112 captures an image of a paper lab report provided by healthcare provider 122. Still, EMRs 147 could adhere to standards for managing EMRs/EHRs; ISO 18308:2011 or IEEE 11073 for interfacing records to medical devices for example.

With respect to the stakeholder being healthcare provider 122 and EMRs 147N being associated with healthcare provider 122, EMRs 147N could be vastly different from those associated with patient 112. Further, healthcare provider 122 could also represent one or more types of healthcare entity: a hospital, a technician, a lab, a nurse, a care giver, a doctor, a specialist, a researcher, or a surgeon just to name a few, which can heavily impact the nature of EMRs 147N. EMRs 147N could include many different types of healthcare provider records, including business accounts, process records, procedure records, workflow documents, transaction histories, employee healthcare records, employer healthcare records, tax records, certifications, compliance records, or other types of records associated with healthcare provider 122.

Although the examples described herein disclose the transaction between patient 112 and healthcare provider 122 via their corresponding devices, it should be appreciated that data record custodian system 100 brokers access or management to any type of healthcare stakeholders having a mobile account with the mobile carrier or with a different mobile carrier having similar capabilities. Thus, a mobile carrier can be considered as the data record custodian and broker.

Patient 112 submits EMR request 152 to mobile account management server 150 via mobile device 110. EMR request 152 can include a request for an EMR. However, it should be appreciated that EMR request 152 is considered to be an electronic request involving or associated with one or more EMRs 147A. In this example, EMR request 152 could be considered a request from patient 112 to send EMRs 147A to healthcare provider 122.

Mobile account management server 150 is configured or programmed to receive EMR request 152 over cellular network interface 130. For example, patient 112 might be at home being attended by healthcare provider 122 taking a blood sample. Patient 112 may use a smart phone operating as mobile device 110 to connect with mobile account management server 150, for example, via a cOS web service interface using HTTP (e.g., XML, JSON, YAML, SOAP, WSDL, etc.) or other cOS protocol to which EMR request 152 adheres. Patient 112 can, via a patient interface (not shown), select one or more of EMRs 147A related to their blood type and send the record to healthcare provider 122.

Just as healthcare provider 122 or patient 112 can represent a wide variety of stakeholders within the ecosystem, EMR request 152 can also take on many different forms depending on its nature. Within the cOS environment, example requests might focus on one or more cOS services. Example cOS service requests could include a monitor service request, an alert request, a workflow request, a business service request, a routing services request, a validation request, a discovery service request, a consent services request, an event services request, or other type of cOS service request. In various embodiments, EMR request 152 can take on a broad spectrum of features including requests including context attributes, attributes for goods, attributes for services, record queries, financial or other transactions information, or other types of features. Mobile account management server 150 attempts to service EMR request 152 by constructing a query targeting EMR database 140 as a function of the features of the request including one or more mobile user accounts.

EMR request 152 could also represent a healthcare services transaction where patient 112 interacts with healthcare provider 122 with respect to one or more healthcare services. In such cases, EMR request 152 can relate to one or more of a request for a service, a location of a service, a cost of a service, a service authorization, a service authentication, a healthcare provider request, a claim adjudication in cases where insurance is involved, or other type of service. As a more specific example we return to the example of healthcare provider 122 drawing blood from patient 112, and patient 112 requires a blood test under orders from a local doctor. Patient 112 constructs EMR request 152 to request that a technician come to the home of patient 112. EMR request 152 might include selections of relevant EMRs 147A, the location of their home, or other contextual information. Mobile account management server 150 can then broker the request to identify which healthcare provider 122 is proximal to patient 112 and would be available or able to service the request for the blood test. Beyond healthcare services, EMR request 152 can also relate to healthcare goods transactions involving one or more healthcare goods. Example transactions associated with goods could include a healthcare product purchase, a prescription, a product lease, or other type of transaction related to a healthcare good. In such cases, EMRs 147 might comprise receipts for such transactions or a record of use.

Yet another type of EMR request 152 could include a record transaction that interacts with EMRs 147 as data objects. The record transactions allow various stakeholders to directly manage or analyze EMRs 147. Example records transactions could include a record write transaction, a record read transaction, a record create transaction, a record delete transaction, a record modify transaction, or other record manipulation. The record transactions also allow remote applications or apps to interact with EMRs 147 assuming proper authentication or authorization is provided by the record owner. To continue the previous example of healthcare provider 122 drawing blood, after the sample is taken, patient 112 could use a camera on their mobile device 110 to capture an image of the blood collection tube and associated codes (e.g., bar code, alpha-numerics, etc.). In view that the blood sample is a new healthcare transaction, mobile device 110 can submit a record create transaction request within EMR request 152 to create a new EMR 147A for patient 112.

Once mobile account management server 150 obtains EMR request 152, it can begin processing the request. Mobile account management server 150 is further configured or programmed to continuing processing the request by querying EMR database 140 for a results set of EMRs 147 satisfying a query. Further, the query can be constructed as a function of the one or more mobile user accounts 145 (e.g., account number, phone number, device ID, GUID, UUID, key, token, etc.). In some embodiments, mobile account management server 150 queries EMR database 140 through submitting the query to EMR database 140, for example, via an API, web service, or through an internal cOS message passing scheme. Query 154 can be instantiated from information with EMR request 152 beyond information related to one or more of mobile user accounts 145. For example, EMR request 152 could include healthcare context data that represents metadata that describes the nature or circumstances under which a current healthcare event is taking place. The healthcare context data could comprise a contextual representation of one or more entities involved within the healthcare event. Depending on the specific scenario, the context data might indicate a specific context associated with mobile device 110, remote device 120, one or more stakeholders, healthcare provider 122, patient 112, a healthcare service, a healthcare product, a location of the event, or other entities. Mobile account management server 150 can compile the context data into query 154 in preparation for submission to EMR database 140. The query can be packaged based on the nature of EMR database 140 and might include an SQL query, a serialized data stream to a web service API, or a direct call to a cOS API.

In response to query 154, EMR database 140 returns results set 156, which can include zero or more EMRs 147 that satisfy query 154. Returning to the blood sample example, results set 156 might include blood type information or previous blood test results. In some embodiments, results set 156 might include information relating to healthcare provider 122; a digital certificate indicating that healthcare provider 122 is certified for drawing blood for example.

Mobile account management server 150 is further configured or programmed to generate EMR response 158 as a function of results set 156. EMR response 158 can be just as varied as EMR request 152 and depends on the nature of the current healthcare event or transaction. In the example shown, EMR response 158 might include an encrypted blood type report. Once healthcare provider 122 is properly authorized by patient 112 or mobile account management server 150, the report can be decrypted and provided to remote device 120 for consumption by healthcare provider 122. Further, mobile account management server 150 can be further configured to generate EMR response 158 as a function of the healthcare context data present in EMR request 152. For example, EMR response 158 can be tailored based on one or more of the following healthcare context attributes: an absolute location (e.g., GPS coordinate, triangulation, RSSI, etc.), a relative location (e.g., distance between patient 112 and healthcare provider 122, etc.), a time, sending device attributes, receiving device attributes, a patient identifier, a healthcare provider identifier, a weather condition, a traffic condition, an urgency, a priority, a certification requirement, a relationship requirement (e.g., known person, family member, etc.), or other attributes.

Mobile account management server 150 is also configured or programmed to transmit EMR response 158 to remote device 120 via cellular network 115. EMR response 158 can be packaged in numerous ways for the transmission. In some embodiments, EMR response 158 can be encrypted, for example based on a public key of healthcare provider 122. Once EMR response 158 is resident in memory of remote device 120, a private key of healthcare provider 122 can be used to decrypt EMR response 158. EMR response 158 could comprise a stream of data that is sent to a secured healthcare data player (e.g., a secure container, a virtual machine, etc.) where the player presents the data within EMR response 158 to healthcare provider 122. Depending on the circumstances of the corresponding healthcare transaction taking place, EMR response 158 could be packaged to accommodate the specific transaction, thereby adhering to corresponding transaction protocols (e.g., HTTP, FTP, HL7, etc.). With respect to the example of healthcare provider 122 taking a blood sample, EMR response 158 might include a JPEG image of a paper copy of a certified or notarized blood test report indicating the blood type of patient 112.

EMR response 158 can be quite complex and represent a synthesis of information derived from EMRs 147. In some embodiments, data record custodian system 100 can also include one or more analytics engines (not shown) that processes data from EMRs 147 to generate a resulting report (e.g., graphs, charts, spreadsheet, etc.). Although patient 112 may be provided with minimal analytics information, healthcare provider 122 may be provided with extensive analytics information. In such cases the analytics engine can be configured or programmed to compile analytics from results set 156 and incorporate the resulting analytics into EMR response 158. From the perspective of patient 112, the analytics might be a simple trend of blood pressure or cholesterol level for example. From the perspective of healthcare provider 122, for example operating as a researcher, the analytics might include a comprehensive analysis within a longitudinal study across large populations of patients; assuming the researcher has been granted access to EMRs 147 of the patients.

The disclosed approach of having a mobile carrier operating as data record custodian system 100 gives rise to numerous capabilities or advantages within a retail or commoditized healthcare market. Consider an example relating to making payments for healthcare transactions. In the retail market, no intermediary healthcare payment services (e.g., insurance, clearing houses, etc.) are required. Rather, mobile account management server 150 is able to handle all payment services. For example patient 112 is traveling away from home and does not have access to a preferred physician located nearby patient 112's home. Patient 112 can submit a request for a local physician with specific skills (i.e., context data) via mobile device 110 to mobile account management server 150. In response, patient 112 could receive a listing, ranked in some embodiments, of physicians (i.e., healthcare provider 122) that are local to patient 112. Further, the physician could receive patient 112's relevant EMRs once authorization has been granted in order to prepare for an appointment. After the physician has rendered services, the physician can submit a bill through mobile account management server 150 to mobile device 110 of patient 112.

In some embodiments, patient 112 can authorize payment in real-time, after which mobile account management server 150 initiates a transaction between the two accounts of healthcare provider 122 and patient 112. Patient 112 can receive the monthly mobile carrier bill, which includes an indication that payment has been made. Patient 112 pays the bill normally as they would any mobile phone bill. In such cases, EMR request 152 can be considered a payment authorization request associated the mobile user accounts 145 or even an actual payment to one or more mobile user accounts 145. In some embodiments, the mobile carrier can host a funded account or pre-paid for patient 112, which allows the mobile carrier to exchange funds without operating as a bank. Such embodiments include production or management of pre-paid healthcare service cards that can be used a points of treatment. A consumer could simply purchase a pre-paid healthcare card, say at a local pharmacy, and activate the card. The card can then be used to initialize a healthcare payment transaction, finalize a transaction, or fund a payment account with the mobile carrier.

Another advantage of the disclosed techniques is that each stakeholder in the ecosystem retains full control and access to corresponding EMRs. The mobile carrier, possibly through a cOS system, could operate in an active mode that is fully aware of the healthcare transactions or could operate as a passive custodian without awareness of the underlying healthcare data. For example in a passive mode of operating, if the mobile carrier provides a homomorphic encryption environment, the mobile carrier merely brokers requests with the environment without actual access or knowledge of the data where the actual data remains secured from the mobile carrier's view. This approach ensures that each stakeholder's data remains secure as well as private. Each mobile device in the ecosystem can also be provisioned to operate as a cOS agent via an app. The cOS agent can configure the mobile device to operate essentially as an I/O device, possibly as a sensor platform, for the broader cOS system. Thus, the agent enables the mobile device to capture data, sense biometric data, sense context data, display data, request data, process data, or otherwise interact with EMRs as needed.

Embodiments of system 100 allow each stakeholder to have separate personal, secured healthcare cloud hosted by the mobile carrier. As stakeholders interact with each other through the mobile carrier, data from respective EMRs can be transferred from one mobile user account to another without exiting the environment and while maintaining integrity of each stakeholder's cloud. In cases where one or more stakeholders exist outside the ecosystem, the mobile account management server can be provisioned with one or more agents capable of converting or translating transaction requests or responses to an appropriate format.

The EMRs can be stored in many data formats in support of the retail nature of the market where EMR data is collected in an unsupervised manner. Therefore, EMRs can be stored as actual electronic documents (e.g., PDFs, etc.), still images, videos, audio data, or other data modalities. The EMR database or mobile account management server could also be provisioned with one or more recognition engines that convert each type of EMR data modality to an internal, normalized format if desired. For example, images of receipts could be processed by an implementation of an optical character recognition (OCR) algorithm to convert the image to text. Audio data could be transcribed through execution of one or more implementations of automatic speech recognition (ASR) algorithms. Still further, images or videos could be analyzed by implementations of object recognition algorithms to identify people, objects, diseases, or other features found within the images.

The disclosed ecosystem also supports machine-to-machine (M2M) communications as brokered by the mobile account management server. One or more medical devices, for example located in remote or rural locations, can be configured or outfitted with a cellular radio or modem to comprise remote device 120. As data is received from remote device 120, the data can be collected by the mobile carrier and inserted into one or more EMRs of corresponding mobile user accounts. For example, remote patient 112 might require active monitoring. Patient 112's cell phone, comprising mobile device 110, might connect via Bluetooth to patient 112's medical monitoring equipment. The collected data is sent to the mobile carrier, which creates corresponding EMRs. Further the collected data could also be sent to patient 112's physician's EMR repository. Rather than using a cell phone as a hub, it is also possible for the medical devices to comprise mobile device 110 and to directly connect with mobile account management server 150, for example where each medical device has its own account and where the device account could be linked to patient 112.

It is also possible that stakeholders might exist on separate mobile carrier platforms. For example, in India patient 112 might use Idea Cellular as the mobile carrier while a healthcare provider might use Bharti Airtel™ or Vodafone®. In a heterogeneous environment, it is possible for each mobile carrier to operate as individual custodians, for example where each mobile carrier is in fact a cOS entity. In such cases, each entity would likely adhere to the cOS service standards or protocols thereby allowing the mobile carriers to broker data exchanges among each other. Data exchanges can occur once suitable authorizations or authentications are established or as necessitated by various factors; a life or death emergency for example. If one of the mobile carriers is not operating as a custodian, then the mobile carrier that does operate as a custodian can receive communications from other entities via traditional mobile communication systems (e.g., SMS, MMS, email, web services, etc.) and archive the communications into the appropriate mobile user account's EMRs.

Although the disclosed approach assumes a retail or commoditized healthcare market where regulatory overhead is less present, regulations or standards still can have a beneficial impact on the ecosystem. Each mobile carrier operating as a data custodian can still adopt known or yet to be created standards to provide trusted services. For example, a mobile carrier in an undeveloped area could adopt one or more features of the Health Insurance Portability and Accountability Act of 1996 (HIPAA) or even Patient Safety and Quality Improvement Act of 2005 (PSQIA) as established in the United States. Such standards or regulations might not apply in jurisdictions outside the United States. However, the features in such standards or regulations still might offer valuable market differentiators for mobile carriers due to at least some level of compliance with externally established standards.

Each jurisdiction could have widely different standards or regulations. The disclosed approach seeks to enable mobile carriers to become medical or healthcare custodians, especially when existing medical or healthcare data infrastructure is lagging deployment of mobile infrastructure, while still adhering to relevant requirements. In India for example, mobile carriers could store mobile user's EMRs based on the user's unique health identifier (UHID) or AADHAR number and while also fulfilling the role of a mobile services delivery gateway for government service. Further, the mobile carriers can integrate cOS service modules that configure the mobile carriers to conform to the various desired standards or protocols (e.g., HL7, CCD, openEHR, IHE, DICOM, etc.).

Yet another interesting aspect of allowing mobile carriers to operate as a healthcare data custodian includes contextually pre-caching EMR data in mobile remote device 120 (e.g., mobile phone). From the perspective of a healthcare provider, healthcare provider's remote device 120 can pre-cache patient 112's records, for example in a secure container (e.g., a virtual machine, etc.) in preparation of a healthcare transaction with patient 112 under the assumption that the healthcare provider has been authorized to request such data or to be provisioned with such data. Consider a scenario where patient 112 requires urgent care, but has restricted movement due to weather or traffic conditions. Mobile account management server 150 receives the request from patient 112 and identifies one or more appropriate healthcare providers 122 within walking distant of patient 112. In response, healthcare provider 112 accepts the request for services from relevant patient EMRs. Further, patient 112 (or the patient's caretaker) can receive healthcare provider 122's identification (e.g., photograph, license information, history, ETA, etc.) in preparation for the corresponding appointment. In embodiments, where the EMR data has been provisioned on the healthcare provider's cell phone and within a secured container, the container can be unlocked when the patient's phone is proximal to the healthcare provider's phone (e.g., within 30 meters, within 20 meters, etc.) based on location information (e.g., GPS, wireless triangulations, etc.). This example illustrates using context data of location, traffic, and/or weather to pre-cache EMR data. Mobile carriers are uniquely able to provide such context-base services because they are able to directly capture mobile device context data as well as broadcast requests to participants in the network.

Context-based caching of EMR data can take on many different forms. In some embodiments, geo-fence boundaries can be established where EMR request management is permitted. Pre-caching can aid in reducing latency between a time of an appointment and a time of rendering a service because healthcare provider 122's remote device 120 can be a priori provisioned with necessary data before services are rendered to patient 112.

When remote device 120 enters the geo-fenced area, remote device 120 can be configured to download (or upload) relevant EMR data to be archived by the mobile carrier. The data can be exchanged with the mobile carrier via the cellular network or through high speed connections (e.g., Ethernet, WiFi, etc.) where available. Geo-fenced areas might include healthcare provider 122's facilities (e.g., hospitals, urgent care, pharmacies, etc.), patient 112's home, a neighborhood, a city, a postal code, a building or floor in a building, or other boundary definition. The boundaries could also depend on context data beyond location. Time can also be used as a contextual boundary where healthcare provider 122 is restricted to have access to patient 112's EMRs only for a limited time surrounding the appointment with patient 112.

Mobile account management server 150 can provide an interactive portable between or among stakeholders. Patient 112 could request a set of services, which are in turn forwarded to contextually relevant healthcare providers 122. Healthcare providers 122 can respond with their qualifications and estimated costs. Patient 112 can select from multiple healthcare providers 122 who have responded. Interestingly, both patient 112 and healthcare provider 122 could access the same relevant EMR data, but interact with the EMR data in substantially different ways. For example, mobile account management server 150 can present a list of relevant EMRs that may be forwarded to healthcare providers 122 upon patient 112's request. The listing of EMRs can include a description in layman's terms of the relevance of the documents. When selected healthcare provider 122 receives the documents, the data or documents can be translated into a technical description. Thus, the mobile carrier operates as a translation service to present the EMR data in a manner that is conducive to each stakeholder's needs.

Embodiments of system 100 can facilitate a healthcare market that operates according to different regulations, standards, or other requirements. In less regulated markets, healthcare goods or services can become heavily commoditized, or even treated as retail goods or services, thereby reducing efficacy of multi-party data management systems. Further, patient 112 can assume a more intimate role in managing patient 112's own healthcare data. Embodiments of system 100 can provide patient 112 with additional tools for storing, accessing, managing, or otherwise interacting with patient 112's own healthcare data. In various embodiments, patient 112's mobile device 110 can operate as a personal portal to healthcare data where the mobile carrier can further operate as an active or passive data custodian through which patient 112's EMR can be stored or accessed.

A mobile carrier-centric data record custodian system 100 is presented, which comprises plurality of cellular network interfaces 130 configured to transmit and receive wireless communication over cellular network 115, an EMR database 140 configured to store a plurality EMRs 147 indexed appropriately, for example, according to mobile user accounts 145, and mobile account management server 150 coupled with cellular network interfaces 130 and EMR database 140. Mobile account management server 150 receives EMR request 152 associated with at least one mobile user account 145A over cellular network 15, queries EMR database 140 for results set 156 having EMRs 147 satisfying the query and as a function of mobile user account 145A, generates a plurality of EMR responses 158 to EMR request 152 as a function of results set 156 and state information associated with mobile device 110 (and/or remote device 120), cellular network 115, and mobile user account 145A, and transmits plurality of EMR responses 158 over cellular network interfaces 130 to mobile device 110 (and/or remote device 120) via cellular network 115, each one of EMR responses 158 being formatted for a specific wireless protocol corresponding to a respective cellular network interface 130 over which it is transmitted.

Each cellular network interface 130 couples with one or more of various wireless networks, including GSM, EDGE, HSPA, HSPA+, TD-LTE, CDMA, UMTS, WiMAX, EVDO, and WiFi, with different cellular network interfaces 130 coupling with correspondingly different wireless networks. Examples of mobile device 110 and remote device 120 include a smart phone, a vehicle, a robot, a tablet, a medical device, a sensor, a device server, a point of sales terminal, a kiosk, a vehicle, and a tablet. Note that in some embodiments, EMR database 140 may be coupled with plurality of cellular network interfaces 130.

In some embodiments, EMR database 140 includes a clinical operating system (cOS) service. In some embodiments, mobile account management server 150 itself includes a clinical operating system. In such embodiments, EMR request 152 adheres to a protocol of the clinical operating system. For example, EMR request 152 can include one or more of a monitoring service request, an alert request, a workflow request, a business service request, a routing services request, a validation request, a discovery service request, a consent services request, and an event services request. Mobile account management server 150 may be further configured to provide access to the clinical operating system via an application program interface (API). The API may be published via at least one of plurality of cellular network interfaces 130. In some embodiments, the API may include a web service API.

In some embodiments, EMR request 152 may include a healthcare services transaction, for example, a request for a service, a location of a service, a cost of a service, a service authorization, a service authentication, a healthcare provider request, and a service adjudication. In some embodiments, EMR request 152 may include a healthcare goods transaction, for example, a healthcare product purchase, a prescription, and a healthcare product lease. In some embodiments, EMR request 152 may include a records transaction, for example, a record write transaction, a record read transaction, a record create transaction, a record delete transaction, and a record modify transaction.

In some embodiments, EMR request 152 may include healthcare context data, for example, including a contextual representation of mobile device 110 (and/or remote device 120), patient 112, healthcare provider 122, a service (e.g., diagnosis), a product (e.g., medication), a location (e.g., physician's office), or an event (e.g., hospital admission). In such embodiments, mobile account management server 150 may be configured to generate plurality of EMR responses 158 as a function of the healthcare context data. Examples of healthcare context data includes an absolute location of mobile device 110 (and/or remote device 120), a relative location of mobile device 110 (and/or remote device 120), a time of EMR request 152 (e.g., time of receipt at mobile account management server 150), a patient identifier, a healthcare provider identifier, a weather condition at a location of mobile device 110 (and/or remote device 120), a traffic condition around a location of mobile device 110 (and/or remote device 120), an urgency, a priority, a certification requirement, a relationship requirement, etc.

In some embodiments, EMRs 147 include patient records. In other embodiments, EMRs 147 include healthcare provider records. In yet other embodiments, EMRs 147 include employer healthcare records. In yet other embodiments, EMRs 147 include employee healthcare records. In some embodiments, at least one of EMR responses 158 includes a payment authorization request associated with mobile user account 145A. In other embodiments, at least one of EMR responses 158 can include a payment to an account associated with mobile device EMRs 110 (and/or remote device 120).

In some embodiments, EMR database 140 may be configured to store the plurality of EMRs 147 according to a secured format, for example, that adheres to a cryptographic standard and depends on settings of mobile user account 145A. The secured format may also, or alternatively, adhere to a secure function that depends on a patient's authentication key. In some embodiments, the secured format may include a homomorphic encryption format. In some embodiments, an analytics engine may be coupled with mobile account management server 150, for example, to compile analytics based on results set 156 and in such cases, plurality of EMR responses 158 may include the analytics.

Turning to the infrastructure of system 100, the network topology of the networks used therein, including cellular network 115 can include any number of servers, routers, gateways, base stations, and other nodes inter-connected to form a large and complex network. A node may be any electronic device, client, server, peer, service, application, or other object capable of sending, receiving, or forwarding information over communications channels in a network. Elements of FIG. 1 may be coupled to one another through one or more interfaces employing any suitable connection (wired or wireless), which provides a viable pathway for electronic communications. Additionally, any one or more of these elements may be combined or removed from the architecture based on particular configuration needs.

System 100 may include a configuration capable of Transmission Control Protocol/Internet Protocol (TCP/IP) communications for the electronic transmission or reception of data packets in a network. Healthcare monitoring system 100 may also operate in conjunction with a User Datagram Protocol/Internet Protocol (UDP/IP) or any other suitable protocol, where appropriate and based on particular needs. In addition, gateways, routers, switches, and any other suitable nodes (physical or virtual) may be used to facilitate electronic communication between various nodes in the network.

Note that the numerical and letter designations assigned to the elements of FIG. 1 do not connote any type of hierarchy; the designations are arbitrary and have been used for purposes of teaching only. Such designations should not be construed in any way to limit their capabilities, functionalities, or applications in the potential environments that may benefit from the features of system 100. It should be understood that system 100 shown in FIG. 1 is simplified for ease of illustration.

The example network environment may be configured over a physical infrastructure that may include one or more networks and, further, may be configured in any form including, but not limited to, local area networks (LANs), wireless local area networks (WLANs), virtual local area networks (VLANs), metropolitan area networks (MANs), wide area networks (WANs), virtual private networks (VPNs), Intranet, Extranet, any other appropriate architecture or system, or any combination thereof that facilitates communications in a network.

In some embodiments, a communication link may represent any electronic link supporting a LAN environment such as, for example, cable, Ethernet, wireless technologies (e.g., IEEE 802.11x), ATM, fiber optics, etc. or any suitable combination thereof. In other embodiments, communication links may represent a remote connection through any appropriate medium (e.g., digital subscriber lines (DSL), telephone lines, T1 lines, T3 lines, wireless, satellite, fiber optics, cable, Ethernet, etc. or any combination thereof) and/or through any additional networks such as a wide area networks (e.g., the Internet).

In various embodiments, mobile account management server 150 can include computer executable instructions stored on one or more non-transitory computer-readable media (e.g. hard drives, optical storage media, flash drives, ROM, RAM, etc.) that, when executed by one or more processors, cause the processors to execute the functions and processes described herein. In some embodiments, some functionalities of mobile account management server 150 may be implemented in a distributed manner throughout various networks.

Figure 2:
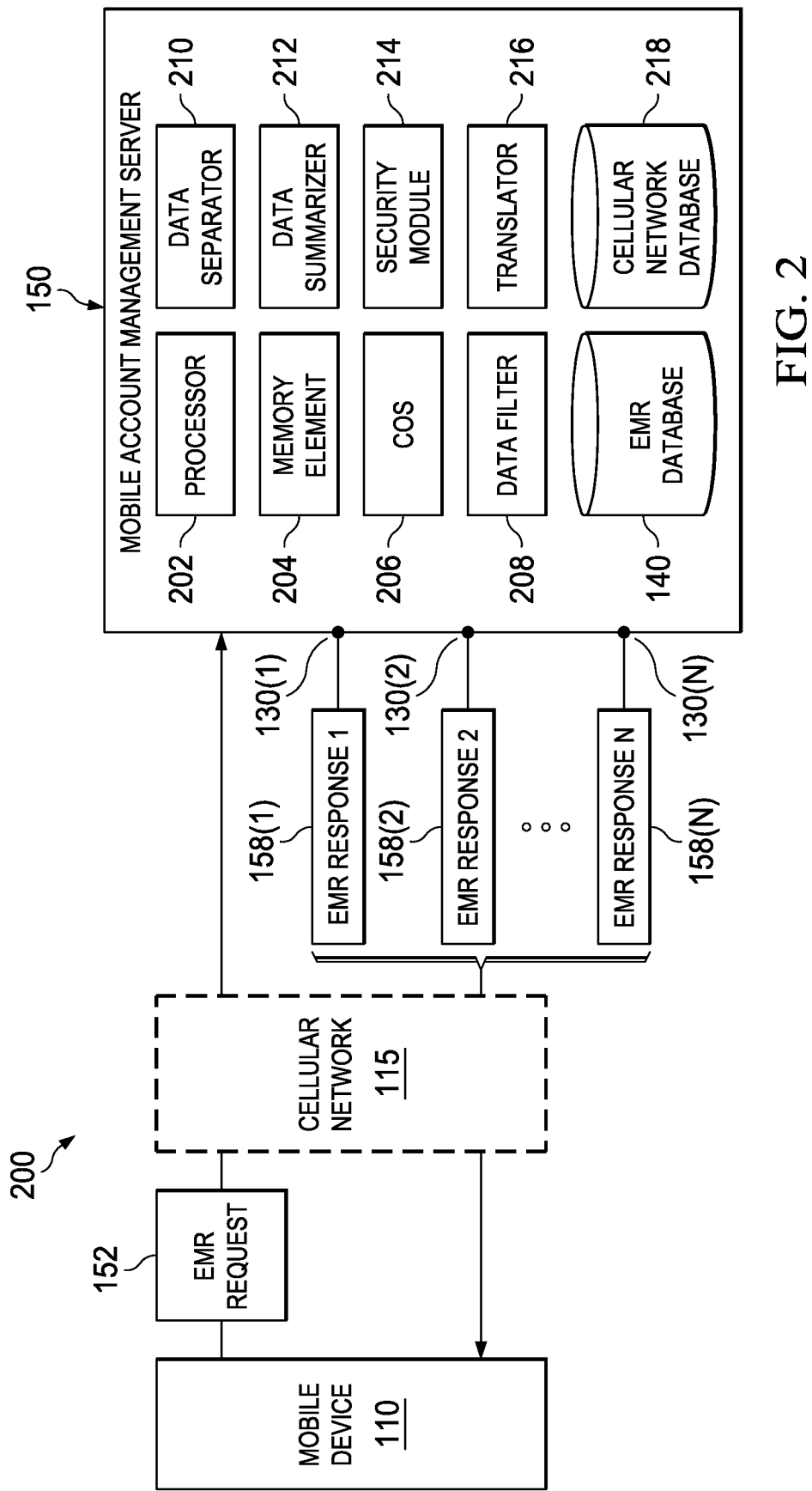
FIG. 2 is a simplified block diagram illustrating example details of the system according to an embodiment.

Turning to FIG. 2, FIG. 2 is a simplified block diagram illustrating a system 200 for facilitating mobile carrier centric data custodians. Mobile device 110 may send EMR request 152 to cellular network 115 (e.g., using a specific destination phone number, SMS number, Internet Protocol (IP) address, or other identifier). EMR request 152 may include a request to access, extract, change, or add data to a specific patient's EMR. In some embodiments, EMR request 152 may include authentication information; in other embodiments, EMR request 152 may be self-authenticated (e.g., any request from particular mobile device 110 associated with specific mobile user may be automatically authenticated to access data of patient 112). Cellular network 115 may direct EMR request 152 to mobile account management server 150. In various embodiments, components of cellular network 115, including base stations, routers, mobility management entities, gateways, etc., may be configured to identify EMR request 152 and direct it to mobile account management server 150 appropriately.

In some embodiments, mobile account management server 150 may include a processor 202 and a memory element 204. Mobile account management server 150 may be further configured with cOS 206, a data filter 208, a data separator 210, a data summarizer 212, a security module 214, a translator 216, a cellular network database 218, and a plurality of cellular network interfaces 130(1)-130(N). In various embodiments, cOS 206 may include a suitable operating system (or platform, or other appropriate software) that can federate various disparate data (e.g., from health providers, patients, sensors, other medical devices, etc.), aggregate the data in disparate formats to a uniform format (e.g., XML based format), and store the uniformly formatted data in a suitable data store (e.g., federated centralized database; data store for aggregated data) such as EMR database 140. cOS 206 may comprise a plurality of self-contained interconnected modules and service layers for connecting proprietary (and public) systems together and extracting and translating data therefrom to enable them to cooperate in a software ecosystem while allowing flexible connections with both existing and new applications. cOS 206 may offer a secure communication tunnel for mobile account management server 150 to interface with mobile device 110.

In various embodiments, cOS 206 may include a plurality of application services and a services module. The application services may be configured or programmed to provide authoritative information (e.g., patient identifier, health provider identifier, etc.), including demographic information associated with a cOS context, and associated with their respective services. In some embodiments, data filter 208, data separator 210, data summarizer 212, and translator 216 may comprise a part of the application services. The services module may be configured with an application services layer configured to handle security of the plurality of application services via security module 214.

Security module 214 may encrypt messages provided by the application services based on a public key infrastructure standard in some embodiments. In some embodiments, the messages can include information obtained from EMR request 152. For example, EMR request 152 may be filtered by data filter 208 to parse and extract information relevant to EMRs stored in EMR database 140; the extracted information may be formatted into a secure message that may be transmitted to EMR database 140; the relevant information may be accessed from EMR database 140 and transmitted securely, by security module 214 to data separator 210.

In various embodiments, cOS 206 may convert EMR request 152 into a markup language message via a message adapter within the services module. In some embodiments, translator 216 may comprise the message adapter. cOS 206 may provide (e.g., via a consent services layer), access to a portion of the requested EMR data according to role-based privacy constraints based on the markup language message, and return a response message, via the message adapter, relating to the requested portion of patient 112's EMR data. The role-based privacy constraints may comprise HIPAA mandated constraints, and may be determined from a deep packet inspection of the message, for example, by the message adapter, or security module 214. In some embodiments, cOS 206 may comprise a clinical file system (CFS) in which data is stored in a particular CFS format. For example, EMR database 140 may store EMRs in the CFS according to the CFS format. For example, prior to storing EMR data in EMR database 140, the EMR data may be normalized according to the CFS format.

In various embodiments, cellular network database 218 may include information related to the state of cellular network 115, including network elements and their configuration in cellular network 115, network routes that are congested, base stations that are off the air, shortest paths to mobile device 110, bandwidth characteristics of cellular network 115, radio resources provisioned for communication with various subscribers, including mobile device 110, service level agreements with mobile user accounts specifying quality of service (QoS) requirements to corresponding communication sessions of the mobile account holders, etc. Cellular network database 218 may also include device information of subscriber devices, including device configuration, capabilities, etc. State information in cellular network database 218 may be dynamic, being updated frequently (e.g., in real-time, when conditions change, etc.), based on particular configuration settings.

In various embodiments, cellular network interfaces 130(1)-130(N) may present physical or logical interfaces to transmit and receive data at mobile account management server 150. Each cellular network interface 130(1)-130(N) may be controlled by corresponding wireless network interface controllers (e.g., IEEE 802.11 adapters, network interface cards, etc.) and device drivers in mobility account management server 150. For example, cellular network interface 130(1) may exclusively receive and send short message service (SMS) text messages or small data over cellular network 115; cellular network interface 130(2) may exclusively receive and send audio messages over cellular network 115; cellular network interface 130(N) may exclusively receive and send large sized data over cellular network 115. In another example, cellular network interface 130(1) may preferably receive and send SMS text messages or small data over cellular network 115 and may also receive and send other types of messages. Any specific communication that includes a mix of several types of messages, for example, audio and data, may be sent over more than one cellular network interface 130(1)-130(N) in some embodiments. N can comprise any suitable integer appropriate to the number of network interfaces for mobile account management server 150. In some embodiments, each of cellular network interfaces 130(1)-130(N) may connect to different network segments in cellular network 115. For example, cellular network interface 130(1) may receive and send SMS text messages over a network route in cellular network 115 that is optimized for SMS text messages; cellular network interface 130(2) may receive and send audio messages over another network route in cellular network 115 that is optimized for audio messages A determination of which cellular network interface 130(1)-130(N) is to be used to send any message from mobile account management server 150 may be based on state information stored in cellular network database 218.

During operation, mobile account management server 150 may receive EMR request 152 from mobile device 110. Data filter 208 may filter out information relevant to EMRs stored in EMR database 140 and generate a query to EMR database 140. A relevant query response may be retrieved from EMR database 140. Data separator 210 may query cellular network database 218, obtain relevant state information of cellular network 115, and separate the retrieved query response into different messages according to different communication protocols based on the obtained state information.

For example, the retrieved query response may comprise a set of high definition X-ray images of different organs of patient 112 taken at different times. The high definition X-ray images may include metadata identifying the time when the X-ray image was taken, the specific organ corresponding to the X-ray image, and the prescribing physician. Data separator 210 may determine from the state information that cellular network 115 is congested near mobile device 110; mobile user account associated with mobile device 110's is subscribed to an SLA that does not permit large volume data in one message; mobile device 110 is not capable of accepting large sized messages; or mobile device 110 cannot interpret messages in certain formats; etc. Data separator 210 may separate the retrieved query response into a plurality of messages, each of which can be transmitted wirelessly over cellular network 115 with low signal degradation, low packet loss, low latency, etc., and which can be received by mobile device 110 and interpreted in a manner useful to the operator (e.g., patient 112, healthcare provider 122) associated with mobile device 110. For example, data separator 210 may separate the retrieved query responses into two messages: a first message comprising an SMS text with the metadata; and a second (or multiple) e-mail message with an attachment comprising large volume data of the high-definition X-ray images.

Data summarizer 212 may parse the messages and summarize relevant information based in deep packet inspection, contextual learning, and other heuristic mechanisms. For example, in the X-ray example, data summarizer 212 may parse the first and second messages, summarize the information contained therein, and generate respective message headers indicative of a context of the message. The SMS text may include a message header identifying that the SMS text is responsive to EMR request 152 and includes metadata of the X-ray images; the large volume data may comprise the e-mail message identifying the attachments separately with links in the body of the e-mail, or other relevant user tools to enable accessing and viewing the X-ray images.

In some embodiments, translator 216 may translate the messages into a format recognizable by mobile device 110 and communicable over cellular network 115. Security module 214 may further encrypt the messages and generate appropriate EMR response 158(1)-158(N). In some embodiments, the encryption may comprise a transaction to authenticate EMR request 152, for example, based on finger printing or face recognition, to allow access to the requested EMR data; if the user's finger print is authenticated, EMR response 158(1)-158(N) may be encrypted accordingly and transmitted to mobile device 110. In another example, image-based recognition (e.g., face, iris, etc.) via mobile device 110 may be used for security and authentication to allow access to the requested EMR data; if the user's image print is recognized, EMR response 158(1)-158(N) may be encrypted accordingly and transmitted to mobile device 110. In yet another example, genomic recognition may be used for authentication. Various other encryption and security measures may be implemented within the broad scope of the embodiments.

Each EMR response 158(1)-158(N) may comprise a message in a particular wireless network protocol format compatible with one of cellular network interfaces 130(1)-130(N). Mobile account management server 150 may transmit EMR response 158(1)-158(N) responsive to EMR request 152 through corresponding cellular network interfaces 130(1)-130(N) to mobile device 110. In various embodiments, mobile account management server 150 may generate a plurality of EMR responses 158(1)-158(N) in response to EMR request 152 based on state information of cellular network 115, including bandwidth conditions of cellular network 115, capabilities of mobile device 110, and service level agreements (SLAs) of mobile user accounts associated with mobile device 110, and transmit EMR responses 158(1)-158(N) through appropriate cellular network interfaces 130(1)-130(N). Thus, mobile account management server 150 may facilitate ensuring that requested EMRs 147 are delivered to mobile device 110 over cellular network 115 with minimal or no packet loss, low signal degradation and low latency, irrespective of the size of requested EMRs 147. Various operations as described herein executed at mobile account management server 150 may ensure an improvement in wireless technologies, for example, facilitating low-loss, low-latency transmission of requested EMRs 147 over cellular network 115, and transmission suited to the receiver's (e.g., mobile device 110) receiving capabilities and requested EMRs 147's characteristics.

Figure 3:
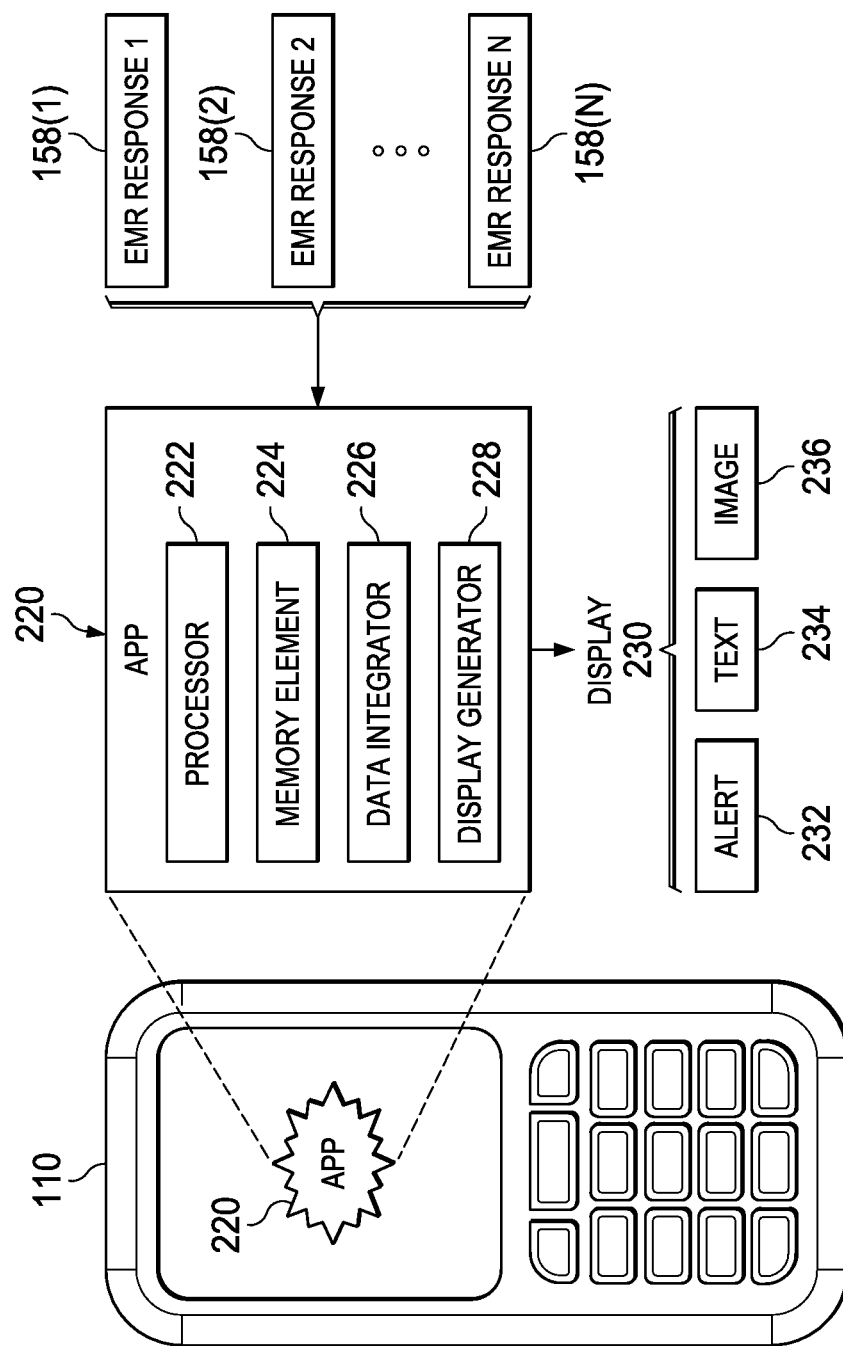
FIG. 3 is a simplified block diagram illustrating example details of the system according to an embodiment.

Turning to FIG. 3, FIG. 3 is a simplified block diagram illustrating example details of an application ('app') 220. App 220 may execute using a processor 222 and a memory element 224 in mobile device 110. App 220 may include a data integrator 226 and a display generator 228. EMR responses 158(1)-158(N) may be received at mobile device 110. Data integrator 226 may integrate EMR responses 158(1)-158(N) into a comprehensible and single message. Display generator 228 may translate the single message into a suitable display 230, which may include sounding an alert 232, displaying a text 234, and/or displaying an image 236 (which can include a video, if appropriate). In some embodiments, EMR responses 158(1)-158(N) may include the application programming interfaces (APIs) relevant to generating the single message and display 230.

Figure 4:
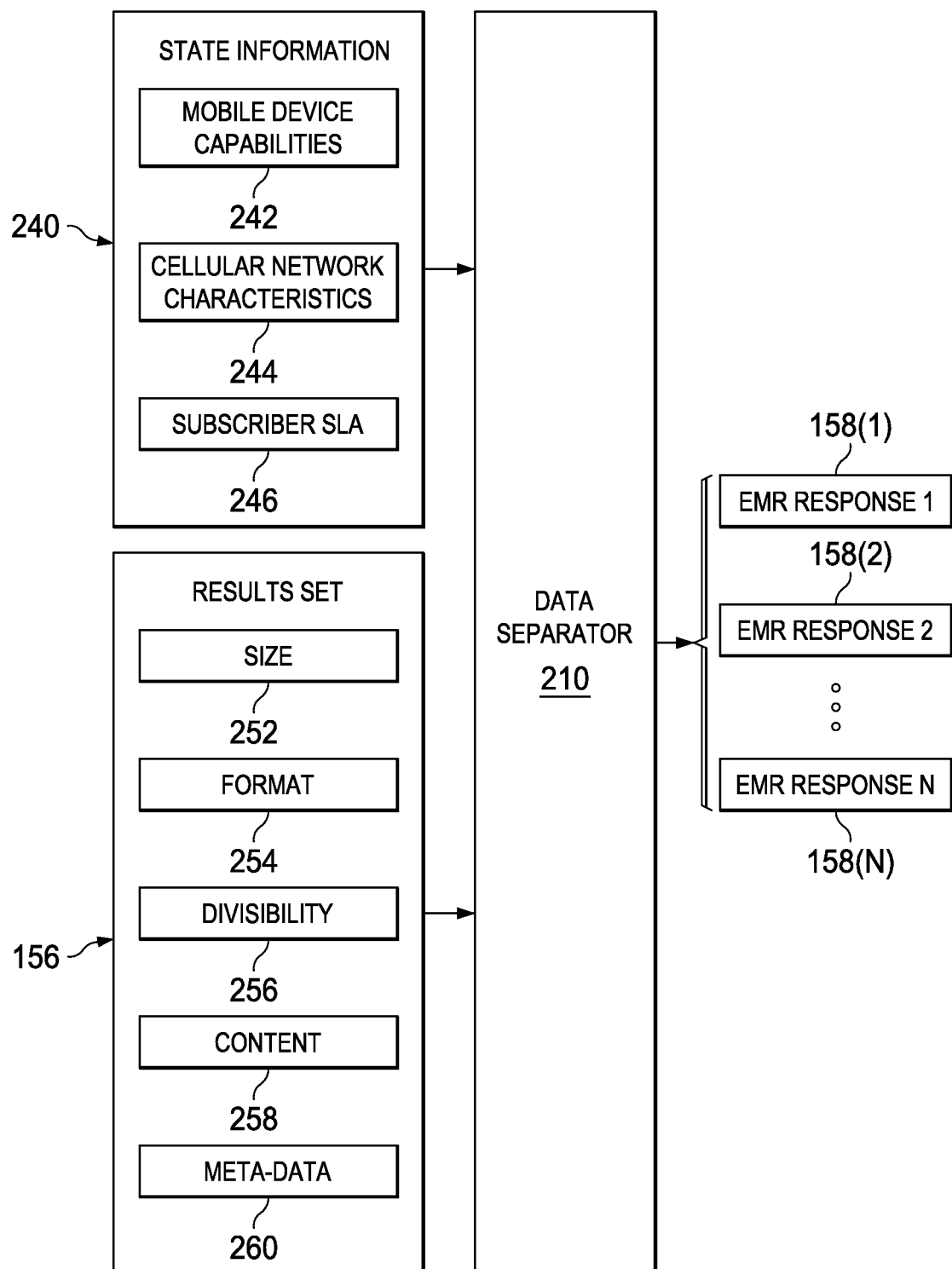
FIG. 4 is a simplified block diagram illustrating example details of the system according to an embodiment.

Turning to FIG. 4, FIG. 4 is a simplified block diagram illustrating example details of generating EMR response 158 according to an embodiment of system 200. State information 240 stored in cellular network database 218 may include, by way of examples and not as limitations, mobile device capabilities 242, cellular network characteristics 244, subscriber SLAs 246, etc. In some embodiments, mobile device capabilities 242 may include configuration settings of various mobile devices that have accounts with the mobile carrier operating mobile account management server 150. In other embodiments, mobile device capabilities 242 may be obtained from packet header information of EMR request 152. In yet other embodiments, mobile device capabilities 242 may be obtained from network information gleaned from network elements (e.g., mobile management entity, enodeB, etc.) in cellular network 115.

Note that the mobile carrier operating cellular network database 218 and mobile account management server 150 has unique insight into various proprietary network state information, private mobile user accounts information, and various other information that are not generally available to third party users. As such, such proprietary information can place the mobile carrier in a unique position as a data custodian to facilitate low loss, low latency, enhanced wireless communication for health related data over cellular network 115.

Cellular network characteristics 244 can include, by way of examples and not as limitations, bandwidth of various network routes between mobile account management server 150 and requesting mobile device 110; latency of the various network routes; network element configurations of the network elements on the various network routes; and any other characteristics of cellular network 115 that can affect message communication between mobile account management server 150 and mobile device 110. Subscriber SLA 246 can include, by way of examples and not as limitations, the maximum latencies negotiated between the mobile carrier and mobile user account associated with mobile device 110; quality of service considerations for packets communicated to and from mobile device 110; authentication settings for various types of EMR data (e.g., no authentication required where personal information is not included in the EMR response; authentication required irrespective of EMR response content, etc.); etc.

In various embodiments, results set 156 is retrieved from EMR database 140 in response to a query generated according to EMR request 152. In various embodiments, results set 156 may be encrypted, such that the mobile carrier cannot read the contents therein. For example, EMR request 152 may request X-ray images of chest taken between January 2015 and June 2015 for patient 112 having a specific patient identifier. EMR request 152 may be formatted according to suitable wireless protocols. The query generated accordingly comprises a search request for the X-ray images of chest taken between January 2015 and June 2015 for the patient identifier and formatted according to the CFS of EMR database 140.

The data retrieved from EMR database 140 in response to the query comprises results set 156. In a general sense, results set 156 may have various characteristics. By way of examples, and not as limitations, the characteristics may include size 252 (e.g., in bytes), format 254 (e.g., image, text, audio, etc.), divisibility 256 (e.g., amenability to be divided into portions, each of which maintain its semantics); content 258 (e.g., nature of information, such as X-ray image, prescription, physician identifier, blood pressure values, etc.), and meta-data 260 (e.g., information describing data). In various embodiments, although the nature of information may be available to the mobile carrier, the content information, such as the values of blood pressure, or the specific X-ray image characteristics, may be encrypted and unavailable to the mobile carrier.

Data separator 210 may use the various characteristics of results set 156 and state information 240 to determine division of results set 156 into a plurality of EMR responses 158(1)-158(N). Any suitable algorithm may be employed for the determination. For example, EMR responses 158(1)-158 (N) may be generated based on size 252 and format 254 of results set 156 in view of mobile device capabilities 242—if mobile device capabilities 242 indicate that only text messages can be viewed at mobile device 110, and size 252 and format 254 of results set 156 indicate a large sized image, data separator 210 may divide results set 156 into two EMR responses 158(1) and 158(2); EMR response 158(1) may comprise an SMS message alerting mobile device 110 to check e-mails for the image; and EMR response 158(2) may comprise an e-mail message with a hyperlink to a location on mobile account management server 150 where the large sized image may be stored for viewing by the user on a web browser.

Figure 5:
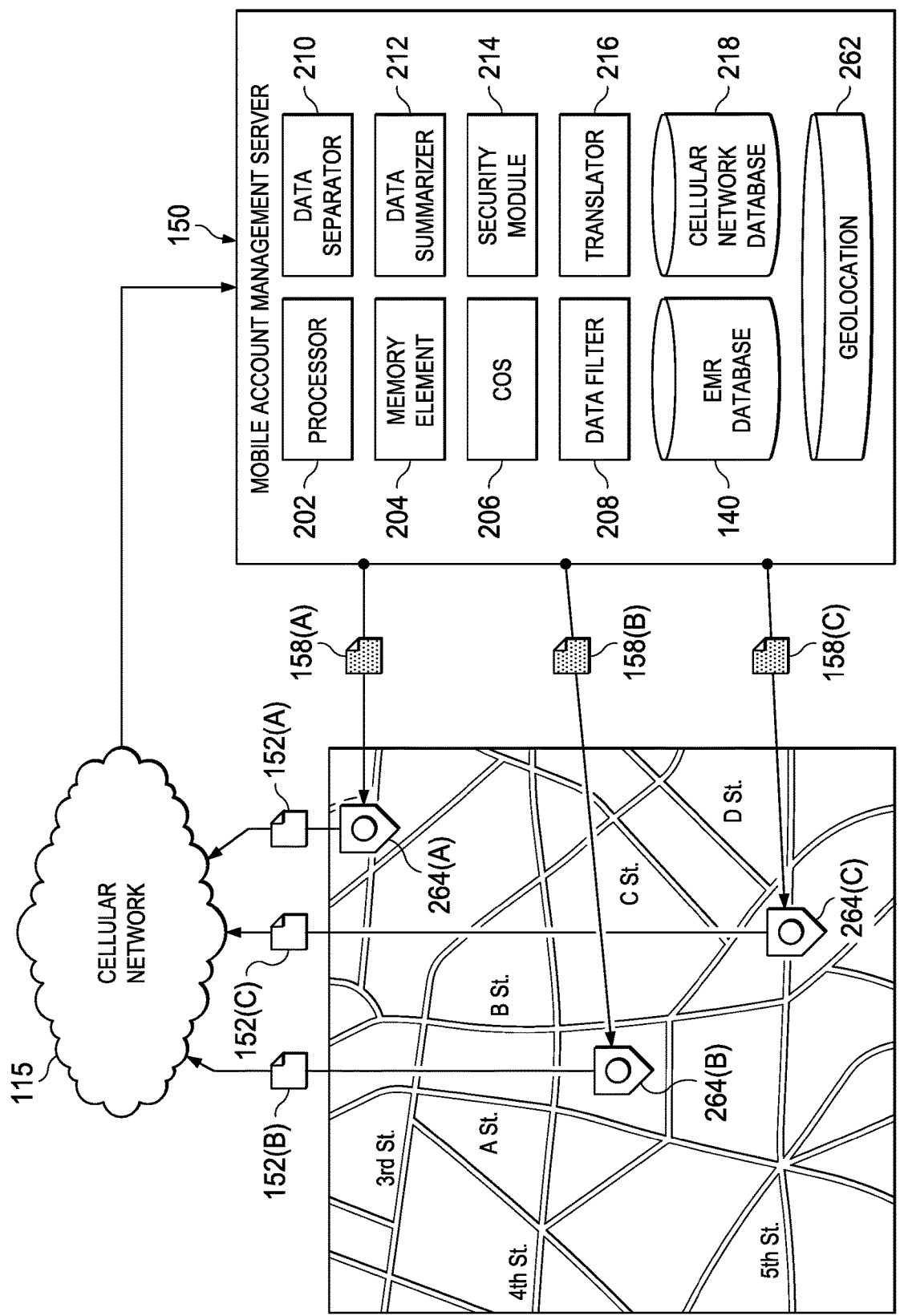
FIG. 5 is a simplified block diagram illustrating example details of the system according to an embodiment.

Turning to FIG. 5, FIG. 5 is a simplified block diagram illustrating example details of geolocation capabilities according to an embodiment of system 200. In various embodiments, mobile account management server 150 may include a geolocation database 262, which comprises various health related location information, for example, physician addresses, hospital addresses, pharmacy locations, nurse practitioner locations, police stations, etc. In various embodiments, location 264 of mobile device 110 may trigger a query of geolocation database 262, and various health related location information relevant to location 264 may be transmitted to mobile device 110 by mobile account management server 150.

Consider, for example, that mobile device 110 is located at a first location 264(A) corresponding to a physician location. EMR request 152(A) sent from location 264(A) over cellular network 115 triggers a lookup of geolocation database 262 at mobile account management server 150. Assume, merely for example purposes, that EMR request 152(A) comprises an update to a particular patient's EMR data including a diagnosis of pneumonia, an antibiotics prescription and an X-ray order. EMR response 158(A) generated and sent by mobile account management server 150 includes, in addition to an acknowledgement of the update, information about radiology laboratories and pharmacies located close to location 264(A).

Assume, merely for example purposes that mobile device 110 moves to location 264(B), corresponding to a location near a radiology laboratory. EMR request 152(B) sent from location 264(B) over cellular network 115 triggers a lookup of geolocation database 262 at mobile account management server 150. Assume, merely for example purposes, that EMR request 152(B) comprises an "I am here" information update; EMR response 158(B) generated and sent by mobile account management server 150 includes, in addition to an acknowledgement of the update, a reminder to take the ordered X-ray at the nearby radiology laboratory.

Assume, merely for example purposes that mobile device 110 moves to location 264(C), corresponding to a location of a pharmacy. EMR request 152(C) sent from location 264(C) over cellular network 115 triggers a lookup of geolocation database 262 at mobile account management server 150. Assume, merely for example purposes, that EMR request 152(C) comprises a request for the prescription updated from location 264(A). EMR response 158(C) generated and sent by mobile account management server 150 includes, in addition to the requested prescription, information about allergies, alternate pharmacies located nearby should the pharmacy not carry the prescribed medication, and other location relevant information. Note that responses 158(A)-158(C) may each include a plurality of EMR responses 158(1)-158(N) that are responsive, in totality, to respective EMR requests 152(A)-152(C) and are individually optimized for wireless transmissions over cellular network 115 to an appropriately receptive mobile device 110.

Figure 6:
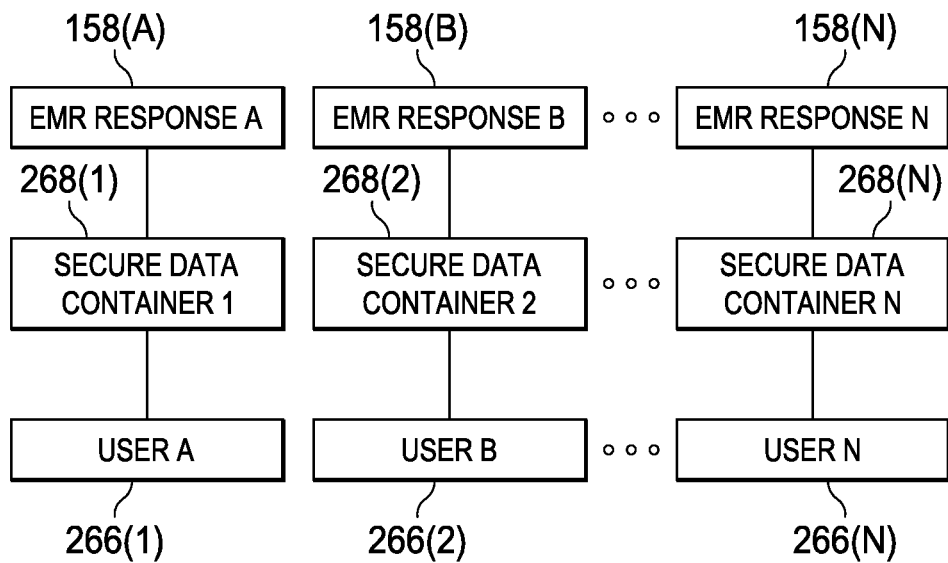
FIG. 6 is a simplified block diagram illustrating example details of the system according to an embodiment.

Turning to FIG. 6, FIG. 6 is a simplified block diagram illustrating example details of an embodiment of system 200. Assume, merely for example purposes and not as a limitation that a plurality of users 266(1)-266(N) are interested in various portions of EMRs 147 pertaining to a specific patient (or patient identifier). For example, a physician may be interested in most recent diagnosis of the patient; a hospital may be interested in the most recent hospital visit of the patient; a pharmacy may be interested in the most recent prescription delivered to the patient; and so on. According to an example embodiment, users 266(1)-266(N) may each be associated with a unique secure data container 268(1)-268(N) at mobile device 110. Secure data containers 268(1)-268(N) may comprise separate authenticated, encrypted portions of memory element 224 in mobile device 110. Each secure data container 268(1)-268(N) may correspond to separate EMR responses 158(A)-158(N); each EMR response 158 comprising a plurality of EMR responses differentiated according to optimized wireless transmissions over cellular network 115 and other parameters.

In various embodiments, the mobile device user, for example, patient 112 may control display of, or access to, information presented in each separate secure data container 268(1)-268(N). For example, patient 112 may present information in secure data container 268(1) to her physician at a doctor's visit; patient 112 may present information in secure data container 268(2) to the hospital care providers at a hospital admission; and patient 112 may present information in secure data container 268(N) to the pharmacy when a prescription is being filled. Various embodiments of system 200 facilitate patient 112 being in control of patient 112's health records at all times.

Figure 7:
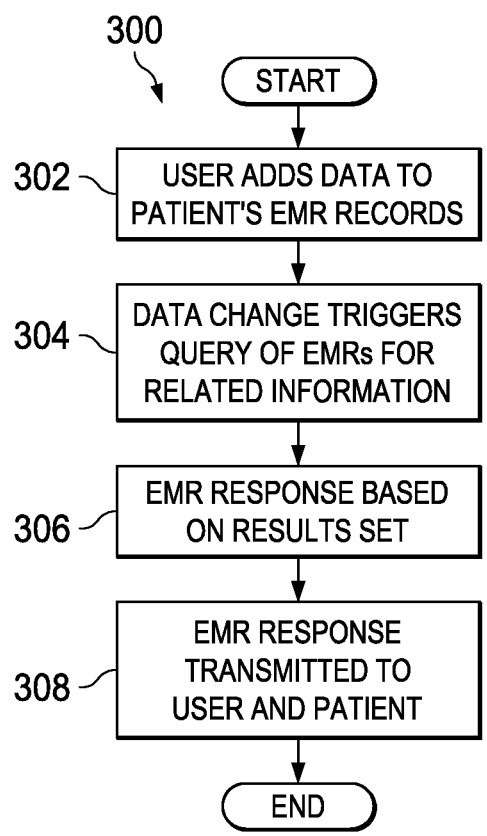
FIG. 7 is a simplified flow diagram illustrating example operations that may be associated with an embodiment of the system.

Turning to FIG. 7, FIG. 7 is a simplified flow diagram illustrating example operations 300 that may be associated with an embodiment of system 200. At 302, a user (e.g., healthcare provider 122) adds data to patient 112's EMRs 147 in EMR database 140, for example, through an appropriate EMR request 152. For example, the update could comprise a prescription for patient 112. At 304, the data change triggers a query of EMRs 147 for information related to the update. For example, the query may seek allergy information relevant to the prescription for patient 112. At 306, EMR response 158 may be based on the returned query response, comprising results set 156. For example, EMR response 158 may comprise allergy information retrieved from patient 112's EMRs 147 and relevant to the prescription. At 308, EMR response 158 may be transmitted to the user (e.g., healthcare provider 122) and patient 112 (e.g., for informational purposes).

Figure 8:
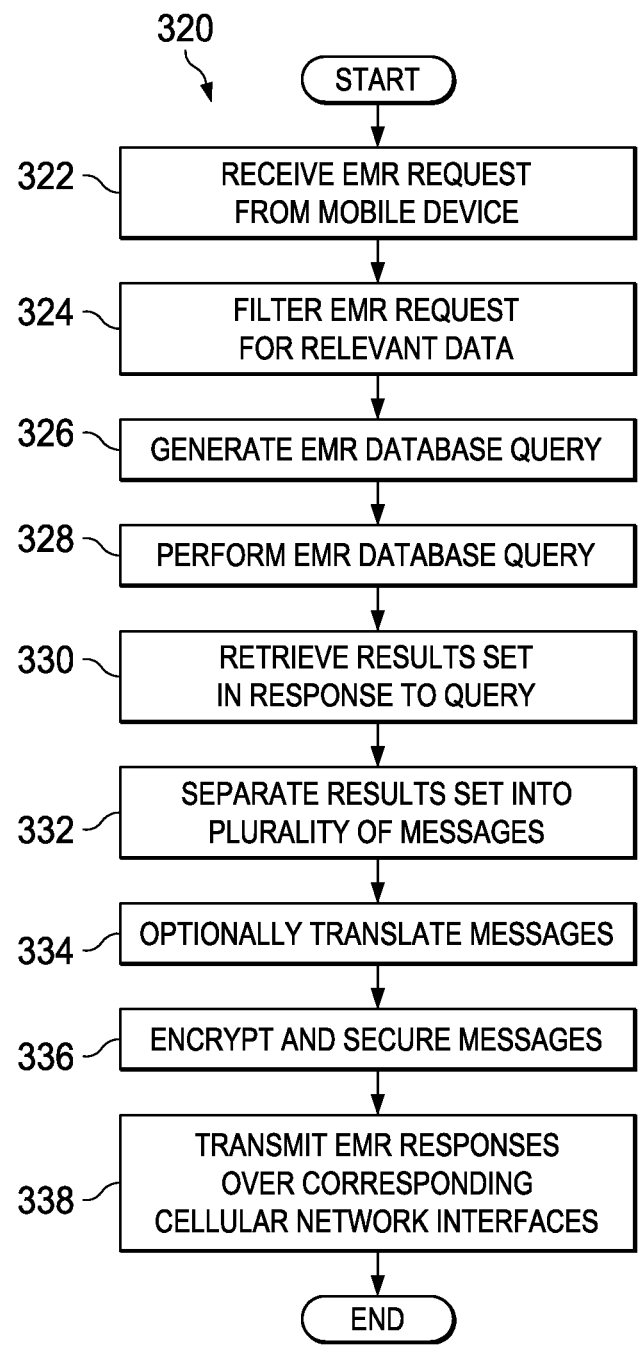
FIG. 8 is a simplified flow diagram illustrating other example operations that may be associated with an embodiment of the system.

Turning to FIG. 8, FIG. 8 is a simplified flow diagram illustrating example operations 320 that may be associated with an embodiment of system 200. At 322, mobile account management server 150 may receive EMR request 152 from mobile device 110 over cellular network 115. At 324, mobile account management server 150 may filter EMR request 152 for relevant data. For example, the filter may extract patient identifiers, medically relevant information (such as prescription information, diagnosis, etc.), location information, etc. At 326, mobile account management server 150 may generate an internal query for the filtered information in EMR database 140. At 328, mobile account management server 150 may perform the query over EMRs 147 stored in EMR database 140. At 330, mobile account management server 150 may retrieve results set 156 in response to the query.

At 332, mobile account management server 150 may separate results set 156 into a plurality of messages based on various parameters, including characteristics of EMR response 250 and state information 240 stored in cellular network database 218. At 334, mobile account management server 150 may optionally translate the messages, for example, in semantics appropriate for the recipient. At 336, mobile account management server 150 may encrypt and secure the messages using appropriate authentication, encryption and security protocols to generate EMR responses 158(1)-158(N). At 338, mobile account management server 150 may transmit EMR responses 158(1)-158(N) over corresponding cellular network interfaces 130(1)-130(N) to mobile device 110.

It should be apparent to those skilled in the art that many more modifications besides those already described are possible without departing from the inventive concepts disclosed herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The foregoing discussion provides many example embodiments of systems and methods for mobile centric data custodians. Although each embodiment represents a single combination of various elements, all possible combinations of the disclosed elements are intended to be included in the broad scope of the disclosure. Thus if one embodiment comprises elements A, B, and C, and a second embodiment comprises elements B and D, then the scope of the disclosure is considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, reaction conditions, and so forth, used to describe and claim certain embodiments of the subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the subject matter are approximations, the numerical values set forth in the specific examples are reported as precisely as practicable. The numerical values presented in some embodiments of the subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. No language in the specification should be construed as indicating any non-claimed element essential to practice the subject matter disclosed herein.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. The use of any and all examples, or exemplary language (e.g. "such as") provided with respect to certain embodiments herein is intended merely to better illuminate the invention and does not pose a limitation on the scope of the embodiments otherwise claimed. No language in the specification should be construed as indicating any non-claimed essential.

In example implementations, at least some portions of the activities outlined herein may be implemented in software in, for example, mobile account management server 150. In some embodiments, one or more of these features may be implemented in hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, adapter 16 and various other components described and shown herein (and/or its associated structures) may also include suitable interfaces for receiving, transmitting, and/or otherwise communicating data or information in a network environment. Additionally, some of the processors and memory elements associated with the various nodes may be removed, or otherwise consolidated such that a single processor and a single memory element are responsible for certain activities. In a general sense, the arrangements depicted in the FIGURES may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc. Moreover, all methods described herein can be performed in any suitable order unless otherwise indicated herein or otherwise clearly contradicted by context.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some of example embodiments, one or more memory elements (e.g., memory elements 204, 224, databases 140, 218, 262) can store data used for the operations described herein. This includes the memory element being able to store instructions (e.g., software, logic, code, etc.) in non-transitory media such that the instructions are executed to carry out the activities described in this Specification. These devices may further keep information in any suitable type of non-transitory storage medium (e.g., random access memory (RAM), read only memory (ROM), field programmable gate array (FPGA), erasable programmable read only memory (EPROM), EEPROM, etc., software, hardware, or in any other suitable component, device, element, or object where appropriate and based on particular needs.

A processor can execute any type of instructions associated with the data to achieve the operations detailed herein in this Specification. In one example, processors (e.g., processors 202, 222) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

The information being tracked, sent, received, or stored in system 100 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Note also that the disclosed subject matter herein enables construction or configuration of an adapter to operate on digital data (e.g., raw sensor data, alarm condition, etc.), beyond the capabilities of a human or un-configured (e.g., off-the-shelf) medical device. Although the digital data can represent sensor data, it should be appreciated that such digital data is a representation of one or more digital models of a patient's medical measurements (and other indicators) and not the measurements (or indicators) themselves, which comprise activities or operations performed by sensors and/or adapters. By instantiation of such digital models in the memory of an adapter, the adapter is able to manage the digital models in a manner that could provide utility to an individual (e.g., a user of the system) that the individual would lack without such a tool.

It should also be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, random access memory (RAM), flash memory, read-only memory (ROM), etc.). The software instructions can configure a suitable computing device to provide the roles, responsibilities, or other functionality as discussed herein with respect to the disclosed apparatus. In some embodiments, the various servers, systems, databases, or interfaces exchange data using standardized protocols or algorithms, possibly based on hyper-text transfer protocol (HTTP), hyper-text transfer protocol secure (HTTPS), Advanced Encryption Standard (AES), public-private key exchanges, web service application programming interfaces (APIs), known financial transaction protocols, or other electronic information exchanging methods. Data exchanges may be conducted over a packet-switched network, the Internet, local area network (LAN), wide area network (WAN), virtual private network (VPN), or other type of packet switched network.

As used in the description herein and throughout the claims that follow, when a system, engine, server, device, module, or other computing element is described as configured to perform or execute functions on data in a memory, the meaning of "configured to" or "programmed to" refers to one or more processors or cores of the computing element being programmed by a set of software instructions stored in the memory of the computing element to execute the set of functions on target data or data objects stored in the memory.

One should appreciate that the disclosed techniques provide many advantageous technical effects including reduction in latency between a computing device ingesting healthcare data and generating a prediction or recommendation. Latency is reduced through storage of health care data in a memory and in the form of N-grams, which can be computationally analyzed quickly.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, system 100 may be applicable to other exchanges or routing protocols. Moreover, although system 100 has been illustrated with reference to particular elements and operations that facilitate the communication process, these elements, and operations may be replaced by any suitable architecture or process that achieves the intended functionality of system 10.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) or (f) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A data record custodian system implemented by a mobile carrier, comprising:

a plurality of cellular network interfaces that transmit and receive wireless communication over a cellular network;

an electronic medical record (EMR) database, coupled with the plurality of cellular network interfaces, that stores a plurality of EMRs indexed at least according to mobile user accounts;

a cellular network database, coupled with the plurality of cellular network interfaces, that stores state information associated with the cellular network, the mobile user accounts, and a plurality of mobile devices, the state information including information about one or more network routes of the cellular network, location information of the plurality of mobile devices, and account terms of the mobile user accounts specifying at least a permitted data volume or data format;

a geolocation database that stores healthcare provider facility location information; and a mobile account management server coupled with the cellular network interfaces, the EMR database, the cellular network database, and the geolocation database, wherein the mobile account management server:

provides, to a first mobile device from among the plurality of mobile devices, access to EMRs associated with at least one mobile user account from among the mobile user accounts in response to the location information stored in the cellular network database indicating that a second mobile device from among the plurality of mobile devices, associated with the at least one mobile user account, is within a predetermined distance of the first mobile device;

receives an EMR request associated with the at least one mobile user account over the cellular network;

queries the EMR database for a results set having EMRs satisfying the EMR request and as a function of the at least one mobile user account;

queries the geolocation database to retrieve healthcare provider facility location information relevant to a location of the second mobile device as determined from the location information stored in the cellular network database;

generates a plurality of EMR responses to the EMR request as a function of the results set, the state information stored in the cellular network database, and the healthcare provider facility location information retrieved from the geolocation database, each one of the plurality of EMR responses being formatted for a specific wireless protocol as a function of the information about the one or more network routes of the cellular network, the location information of the second mobile device, and the account terms of the at least one mobile user account; and transmits the plurality of EMR responses over the plurality of cellular network interfaces to the second mobile device via the cellular network, the specific wireless protocol of each one of the plurality of EMR responses corresponding to a respective cellular network interface over which it is transmitted.

2. The data record custodian system of claim 1, wherein each cellular network interface couples with at least one of the following wireless networks: GSM, EDGE, HSPA, HSPA+, TD-LTE, CDMA, UMTS, WiMAX, EVDO, and WiFi, wherein different cellular network interfaces couples with different wireless networks.

3. The data record custodian system of claim 1, wherein the EMR database comprises a clinical operating system (cOS) service.

4. The data record custodian system of claim 1, wherein the mobile account management server comprises a clinical operating system.

5. The data record custodian system of claim 4, wherein the EMR request adheres to a protocol of the clinical operating system.

6. The data record custodian system of claim 4, wherein the EMR request comprises at least one of the following: a monitoring service request, an alert request, a workflow request, a business service request, a routing services request, a validation request, a discovery service request, a consent services request, and an event services request.

7. The data record custodian system of claim 4, wherein the mobile account management server is further configured to provide access to the clinical operating system via an application program interface (API).

8. The data record custodian system of claim 7, wherein the API is published via at least one of the plurality of cellular network interfaces.

9. The data record custodian system of claim 7, wherein the API comprises a web service API.

10. The data record custodian system of claim 1, wherein the EMR request comprises a healthcare services transaction.

11. The data record custodian system of claim 10, wherein the healthcare services transaction comprises at least one of the following: a request for a service, a location of a service, a cost of a service, a service authorization, a service authentication, a healthcare provider request, and a service adjudication.

12. The data record custodian system of claim 1, wherein the EMR request comprises a healthcare goods transaction.

13. The data record custodian system of claim 12, wherein the healthcare goods transaction comprises at least one of the following: a healthcare product purchase, a prescription, and a healthcare product lease.

14. The data record custodian system of claim 1, wherein the EMR request comprises a records transaction.

15. The data record custodian system of claim 14, wherein the records transaction comprises at least one of the following: a record write transaction, a record read transaction, a record create transaction, a record delete transaction, and a record modify transaction.

16. The data record custodian system of claim 1, wherein the EMR request comprises healthcare context data.

17. The data record custodian system of claim 16, wherein the healthcare context data comprises a contextual representation of at least one of the following: the second mobile device, a patient, a healthcare provider, a service, a product, a location, and an event.

18. The data record custodian system of claim 16, wherein the mobile account management server is further configured to generate the plurality of EMR responses as a function of the healthcare context data.

19. The data record custodian system of claim 16, wherein the healthcare context data includes at least one of the following attributes: an absolute location, a relative location, a time, a patient identifier, a healthcare provider identifier, a weather condition, a traffic condition, an urgency, a priority, a certification requirement, and a relationship requirement.

20. The data record custodian system of claim 1, wherein the EMRs comprise patient records.

21. The data record custodian system of claim 1, wherein the EMRs comprise healthcare provider records.

22. The data record custodian system of claim 1, wherein the EMRs comprise employer healthcare records.

23. The data record custodian system of claim 1, wherein the EMRs comprise employee healthcare records.

24. The data record custodian system of claim 1, wherein at least one of the EMR responses comprises a payment authorization request associated with the mobile user account.

25. The data record custodian system of claim 1, wherein at least one of the EMR responses comprises a payment to an account associated with the second mobile device.

26. The data record custodian system of claim 1, wherein the EMR database is further configured to store the plurality of EMRs according to a secured format.

27. The data record custodian system of claim 26, wherein the secured format adheres to a cryptographic standard and depends on the mobile user account.

28. The data record custodian system of claim 26, wherein the secured format adheres to a secure function that depends on a patient's authentication key.

29. The data record custodian system of claim 26, wherein the secured format comprises a homomorphic encryption format.

30. The data record custodian system of claim 1, further comprising an analytics engine coupled with the mobile account management server and configured to compile analytics based on the results set and wherein the plurality of EMR responses includes the analytics.

31. The data record custodian system of claim 1, wherein the second mobile device comprises a smart phone.

32. The data record custodian system of claim 1, wherein the second mobile device includes at least one of the following: a vehicle, a robot, a tablet, a medical device, a sensor, and a device server.

33. The data record custodian system of claim 1, wherein the plurality of mobile devices includes at least one of the following: a point of sales terminal, a kiosk, a vehicle, and a tablet.

34. A method comprising:

providing, to a first mobile device, access to electronic medical records (EMRs) associated with a mobile user account from among a plurality of mobile user accounts in response to location information indicating that a second mobile device associated with the mobile user account is within a predetermined distance of the first mobile device;

receiving an electronic medical record (EMR) request associated with the mobile user account over a cellular network;

querying an EMR database for a results set having EMRs satisfying the EMR request and as a function of the mobile user account, the EMR database storing a plurality of EMRs indexed at least according to the plurality of mobile user accounts;

querying a geolocation database to retrieve healthcare provider facility location information relevant to a location of the second mobile device;

generating a plurality of EMR responses to the EMR request as a function of the results set, the retrieved healthcare provider facility location information, and state information associated with the cellular network, the plurality of mobile user accounts, and a plurality of mobile devices including the first mobile device and the second mobile device, wherein the state information is stored in a cellular network database and includes information about one or more network routes of the cellular network, the location information of the plurality of mobile devices, and account terms of the plurality of mobile user accounts specifying at least a permitted data volume or data format, wherein each one of the plurality of EMR responses is formatted for a specific wireless protocol as a function of the information about the one or more network routes of the cellular network, the location information of the second mobile device, and the account terms of the mobile user account; and transmitting the plurality of EMR responses over a plurality of cellular network interfaces to the second mobile device via the cellular network, the specific wireless protocol of each one of the plurality of EMR responses corresponding to a respective cellular network interface over which it is transmitted.

35. A non-transitory program storage medium on which are stored instructions executable by a processor or programmable circuit to perform operations comprising:

providing, to a first mobile device, access to electronic medical records (EMRs) associated with a mobile user account from among a plurality of mobile user accounts in response to location information indicating that a second mobile device associated with the mobile user account is within a predetermined distance of the first mobile device;

receiving an electronic medical record (EMR) request associated with the mobile user account over a cellular network;

querying an EMR database for a results set having EMRs satisfying the EMR request and as a function of the mobile user account, the EMR database storing a plurality of EMRs indexed at least according to the plurality of mobile user accounts;

querying a geolocation database to retrieve healthcare provider facility location information relevant to a location of the second mobile device;

generating a plurality of EMR responses to the EMR request as a function of the results set, the retrieved healthcare provider facility location information, and state information associated with the cellular network, the plurality of mobile user accounts, and a plurality of mobile devices including the first mobile device and the second mobile device, wherein the state information is stored in a cellular network database and includes information about one or more network routes of the cellular network, the location information of the plurality of mobile devices, and account terms of the plurality of mobile user accounts specifying at least a permitted data volume or data format, wherein each one of the plurality of EMR responses is formatted for a specific wireless protocol as a function of the information about the one or more network routes of the cellular network, the location information of the second mobile device, and the account terms of the mobile user account; and transmitting the plurality of EMR responses over a plurality of cellular network interfaces to the second mobile device via the cellular network, the specific wireless protocol of each one of the plurality of EMR responses corresponding to a respective cellular network interface over which it is transmitted.

36. The data record custodian system of claim 1, wherein said providing access to EMRs includes pre-caching the EMRs in the first mobile device.

37. The data record custodian system of claim 1, wherein said providing access to EMRs includes unlocking the EMRs in the first mobile device.

38. The data record custodian system of claim 29, wherein the EMR database and the mobile account management server are accessible within a homomorphic encryption space where data exchanges adhere to the homomorphic encryption format.

\* \* \* \* \*